(12) United States Patent
Brettschneider et al.

(10) Patent No.: US 10,308,977 B2
(45) Date of Patent: Jun. 4, 2019

(54) DEVICE AND METHOD FOR PROCESSING A BIOLOGICAL SAMPLE AND ANALYSIS SYSTEM FOR ANALYZING A BIOLOGICAL SPECIMEN

(71) Applicant: Robert Bosch GmbH, Stuttgart (DE)

(72) Inventors: Thomas Brettschneider, Leonberg (DE); Jochen Hoffmann, Renningen (DE); Karin Lemuth, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 14 days.

(21) Appl. No.: 15/311,142

(22) PCT Filed: Apr. 29, 2015

(86) PCT No.: PCT/EP2015/059265
§ 371 (c)(1),
(2) Date: Nov. 14, 2016

(87) PCT Pub. No.: WO2015/173016
PCT Pub. Date: Nov. 19, 2015

(65) Prior Publication Data
US 2017/0088880 A1 Mar. 30, 2017

(30) Foreign Application Priority Data

May 15, 2014 (DE) .......... 10 2014 209 188

(51) Int. Cl.
*G01N 21/00* (2006.01)
*C12Q 1/6806* (2018.01)
(Continued)

(52) U.S. Cl.
CPC ...... *C12Q 1/6806* (2013.01); *B01L 3/502715* (2013.01); *B01L 3/502753* (2013.01);
(Continued)

(58) Field of Classification Search
CPC ............ C12Q 1/6806; B01L 3/502715; B01L 3/502753; B01L 2300/087; B01L 2300/12;
(Continued)

(56) References Cited

U.S. PATENT DOCUMENTS 9,512,421 B1* 12/2016 Branch ................. C12N 13/00
2005/0214173 A1* 9/2005 Facer ....................... C12M 1/00
422/400
(Continued)

FOREIGN PATENT DOCUMENTS

DE  10 2006 041 396 A1  3/2008
DE  10 2010 043 030 A1  5/2012
(Continued)

OTHER PUBLICATIONS

International Search Report corresponding to PCT Application No. PCT/EP2015/059265, dated Aug. 3, 2015 (German and English language document) (7 pages).
(Continued)

*Primary Examiner* — Dennis White
(74) *Attorney, Agent, or Firm* — Maginot, Moore & Beck LLP (57) ABSTRACT

A device for processing a biological sample includes a first substrate having a first cavity, a second substrate having a second cavity, a filter element having a plurality of perforations, and an electrically conductive structure. The first cavity forms a first chamber segment of a chamber for accommodating the biological sample. The second cavity forms a second chamber segment of the chamber for accommodating the biological sample. The filter element is formed between the first cavity and the second cavity in order to hold back a plurality of organic cells of the biological sample on the plurality of perforations when the biological
(Continued)

sample moves between the first cavity and the second cavity through the filter element. The electrically conductive structure is arranged on the filter element and is configured to cause lysis of the organic cells and/or to duplicate and/or detect defined segments of exposed DNA.

19 Claims, 6 Drawing Sheets

(51) Int. Cl.
    *C12N 1/06*     (2006.01)
    *C12N 13/00*     (2006.01)
    *B01L 3/00*     (2006.01)
    *C12N 15/10*     (2006.01)
    *G01N 1/40*     (2006.01)

(52) U.S. Cl.
    CPC ............ *C12N 1/066* (2013.01); *C12N 13/00* (2013.01); *C12N 15/1017* (2013.01); *B01L 2200/0631* (2013.01); *B01L 2200/0647* (2013.01); *B01L 2200/10* (2013.01); *B01L 2300/0627* (2013.01); *B01L 2300/0681* (2013.01); *B01L 2300/087* (2013.01); *B01L 2300/0887* (2013.01); *B01L 2300/12* (2013.01); *B01L 2400/0415* (2013.01); *G01N 2001/4088* (2013.01)

(58) Field of Classification Search
    CPC ......... B01L 2200/10; B01L 2300/0627; B01L 2300/0681; B01L 2200/0647; B01L 2200/0631; B01L 2300/0887; B01L 2400/0415; C12N 13/00; C12N 15/1017; C12N 1/066; G01N 2001/4088
    USPC ....................................................... 422/534
    See application file for complete search history.

(56) References Cited

U.S. PATENT DOCUMENTS

| | | | |
|---|---|---|---|
| 2009/0233351 A1* | 9/2009 | Akechi .............. | B01D 19/0031 435/300.1 |
| 2010/0203521 A1* | 8/2010 | Klapperich ....... | B01L 3/502707 435/6.13 |
| 2011/0065101 A1* | 3/2011 | Bell .................. | B01L 3/502753 435/6.19 |
| 2011/0129931 A1 | 6/2011 | Reboud et al. | |
| 2014/0004501 A1* | 1/2014 | Talebpour .............. | C12N 1/066 435/3 |
| 2017/0211128 A1* | 7/2017 | Talebpour ............ | C12Q 1/6806 |

FOREIGN PATENT DOCUMENTS

| | | |
|---|---|---|
| DE | 10 2011 085 371 A1 | 5/2013 |
| DE | 10 2011 086 235 A1 | 5/2013 |
| DE | 10 2012 216 497 A1 | 3/2014 |
| WO | 2008/072968 A2 | 6/2008 |
| WO | 2009/002580 A2 | 12/2008 |
| WO | 2010/141131 A1 | 12/2010 |
| WO | 2012/119128 A1 | 9/2012 |
| WO | WO 2013072110 * | 5/2013 |

OTHER PUBLICATIONS

Kloke et al.; The LabTube—a novel microfluidic platform for assay automation in laboratory centrifuges, Lab Chip, Feb. 3, 2014, pp. 1527-1537, vol. 14, The Royal Society of Chemistry, www.rsc.org/loc.

Nan et al.; Emerging microfluidic devices for cell lysis: a review, Lab Chip, Dec. 3, 2013, pp. 1060-1073, vol. 14, The Royal Society of Chemistry, www.rsc.org/loc.

\* cited by examiner

DEVICE AND METHOD FOR PROCESSING A BIOLOGICAL SAMPLE AND ANALYSIS SYSTEM FOR ANALYZING A BIOLOGICAL SPECIMEN

This application is a 35 U.S.C. § 371 National Stage Application of PCT/EP2015/059265, filed on Apr. 29, 2015, which claims the benefit of priority to Serial No. DE 10 2014 209 188.8, filed on May 15, 2014 in Germany, the disclosures of which are incorporated herein by reference in their entireties.

BACKGROUND

The present disclosure relates to an apparatus for processing a biological sample, a corresponding method and an analysis system for analyzing a biological sample.

Miniaturized microfluidic diagnostic systems, so-called labs-on-a-chip (LOCs) permit the miniaturized and integrated performance of complex fluidic work processes for identifying various pathogens. Many process steps, which otherwise are usually performed manually in a laboratory, are executed in an automated manner on a compact disposable component. In the published LOC systems, the pathogens to be examined are initially filtered and isolated, then broken up or lysed and the DNA is extracted. Subsequently, specific DNA sections are amplified and identified, for example within the scope of a polymerase chain reaction (PCR). These individual processes are performed in spatially separated regions on the LOC and transferred into the next region in an automated manner after each process step. To this end, layer structures made of polymers or silicon are usually used.

SUMMARY

Against this background, the approach presented here presents an apparatus for processing a biological sample, further a method, which is carried out using the apparatus, and an analysis system for analyzing a biological sample in accordance with the following description. Advantageous configurations emerge from the subsequent description.

By way of a layer structure which has a filter structure, which adjoins two partial chambers each having a fluidic interface, and metallic structures, which are preferably embodied on the filter structure, it is possible to provide a microfluidic environment or structure which allows a number of process steps, which is as high as possible, of the processing of organic cells to be performed in a single chamber of an LOC.

In a development, the layer structure proposed herein may have regions equipped with biochemical capture molecules for subsequent detection of target cells. This is advantageous, in particular, if the layer structure is integrated into a microfluidic environment with a flexible membrane.

In accordance with the approach proposed here, suitable procedures for isolation, lysis and, optionally, DNA amplification of cells may be performed in a single compartment. In addition to a lower space requirement on the chip emerging therefrom, the diagnosis process may be significantly simplified as it is no longer necessary to realize locally different conditions on the chip for the respective procedures. By integrating the isolation of cells, lysis and DNA amplification, it is moreover advantageously possible to dispense with a step of DNA extraction or purification since PCR-inhibiting substances such as e.g. hemoglobin may already be flushed away during the filtration. What this may achieve is a shortening of the process time, a reduction and simplification of process steps and a high sensitivity when identifying target cells.

In a sample analysis performed in accordance with the approach proposed here without spatial separation between individual process steps, it is possible to minimize or even completely prevent a loss of the analyte or other adjuvants by way of adsorption at channel walls when transporting the liquids. By dispensing with, or reducing, the transportation of the sample fluid, it is additionally possible to reduce dead volumes and the number of valves and pumps. A higher sensitivity of the analysis may be reached as the pathogens are broken up in the same chamber in which sections of the DNA thereof are also duplicated.

The layer structure, proposed here, made of filter, partial chambers and metallic structures is particularly advantageously producible using standard processes of microsystem technology, in particular on the basis of silicon wafers. As a result thereof, very small structures such as the filter pores may be produced at low costs in a mass-producible manner. The use of silicon is additionally advantageous on account of the high thermal conductivity, as this allows a very homogeneous temperature distribution to be set and, for example, this allows fast cycling of the temperature to be performed within the scope of a PCP, as a result of which the overall process time is greatly reduced. Furthermore, it is possible to dispense with external heating structures as a result of installing electrically conductive layers. This reduces the manufacturing costs of the layer system by the increased outlay accompanying an external supply unit.

Additionally, efficient lysis methods may be used as a result of the electrical structures, for example a lysis with electric fields which, in terms of the required field strength, could only be supplied with much outlay and very high voltages from the outside. Additionally, the combination, presented here, of a silicon part with a polymer microfluidic environment permits the cost-effective use of unit functions such as valves and pumps on the basis of a flexible polymer membrane.

An analysis method designed according to the approach proposed here facilitates a targeted amplification of target cell DNA as only target cells are fixed on the filter membrane and hence are available with a high concentration for the duplication. Less buffer is required for the overall procedure of the method since it is possible to dispense with buffer for e.g. the DNA extraction, the enzymatic lysis, etc. The method presented herein facilitates a faster procedure together with simplified process control.

An apparatus for processing a biological sample is presented, the apparatus comprising the following features:

a first substrate with a first cavity which forms a first chamber portion of a chamber for receiving the biological sample;

a second substrate with a second cavity which forms a second chamber portion of the chamber for receiving the biological sample;

a filter element with a plurality of perforations, the filter element being embodied between the first cavity and the second cavity in order to hold back a plurality of organic cells of the biological sample at the plurality of perforations when moving the biological sample between the first cavity and the second cavity through the filter element; and an electrically conductive structure which is arranged at the filter element and embodied to bring about lysis of the organic cells and/or to duplicate and/or detect defined sections of the exposed DNA.

The apparatus may be part of a diagnostic system used in a medical laboratory for detecting e.g. bacteria, pathogens and tumor cells. However, the apparatus may also be used independently for lysis of organic cells. The first substrate and the second substrate may be connected in a fluid-tight, manner to form the chamber from the first cavity and the second cavity and therefore be understood in combination as a housing for the chamber. The filter element may be formed in the first substrate or, alternatively, in the second substrate and may have arisen in e.g. a suitable etching process, like the cavities as well in order to hold the organic cells back on the perforations of the filter element, a clear dimension of the perforations may be slightly smaller than a diameter of the organic cells from the biological sample which are of interest for a subsequent diagnosis. By holding back the organic cells on the perforations, the organic cells may be separated from unwanted constituents of the biological sample, such as e.g. hemoglobin, or from further cells which are not of interest, and fixed for the further processing. The electrically conductive structure may be arranged on the filter element in such a way that it contacts the filter element and extends over a majority of a main side of the filter element in a plane parallel to the main side of the filter element.

In accordance with an embodiment of the apparatus, the first substrate and the second substrate may at least partly be formed from silicon. In this way, the apparatus may be realized very accurately in terms of dimensions with small tolerances, as a result of which the functionality of the apparatus may advantageously be increased.

Furthermore, the apparatus may comprise a first fluid channel between a main side of the first substrate facing away from the first cavity and the first cavity and a second flow channel between the main side of the first substrate and the second cavity. The first fluid channel and the second fluid channel may be embodied to admit the biological sample into the chamber and/or release it from the chamber. In this way, filling of the chamber with the sample to be processed may be effected in a simple and cost-effective manner. Moreover, the two chamber portions may be used more flexibly by applying a fluid inlet or fluid outlet thereto.

In accordance with a particular embodiment, the second substrate may comprise a first substrate portion comprising the second cavity and a second substrate portion arranged adjacent to a base of the second cavity forming a wall of the chamber. In particular, the first substrate portion may be made of silicon and the second substrate portion may be made of glass in this case. This embodiment firstly offers the advantage of saving costs by virtue of a wall of the second cavity being able to be formed as a simple perforation in the silicon portion and the glass portion forming a base of the second cavity. Secondly, the substrate portion made of glass, arranged on the outside, reveals a view into the interior of the chamber, for example for monitoring processes there.

In accordance with one embodiment, the electrically conductive structure may comprise a first conductor track between a first connection region of the electrically conductive structure and a second connection region of the electrically conductive structure for applying a first voltage between the first connection region and the second connection region, and a second conductor track between a third connection region of the electrically conductive structure and a fourth connection region of the electrically conductive structure for applying a second voltage between the third connection region and the fourth connection region. In particular, the first conductor track may extend in a first meandering structure along the plurality of perforations of the filter element from the first connection region to the second connection region and the second conductor track may extend in a second meandering structure parallel to the first meandering structure along the plurality of perforations of the filter element from the third connection region to the fourth connection region in this case. In addition to applying different voltages to the electrically conductive structure, this embodiment also permits effective heating of the filter element arranged adjacent to the electrically conductive structure.

In one development, the first conductor track may have at least one first conductor track portion and the second conductor track may have at least one second conductor track portion. Here, the first conductor track portion may extend to an edge of the perforation and the second conductor track portion may extend to a further edge of the perforation lying opposite the edge. Thus, an electric field acting over each perforation may readily be built up on the fitter element.

Furthermore, the apparatus may have a compensation layer for compensating voltage between the first conductor track and the second conductor track. Here, the compensation layer may be arranged laterally adjacent to the electrically conductive structure between the first substrate and the second substrate. Using this embodiment, it is possible to easily avoid an unwanted short circuit between the first conductor track and the second conductor track or between the conductor tracks and current-conducting structures possibly surrounding the apparatus.

For electrically contacting the electrically conductive structure, the first substrate may have a first feedthrough between the main side of the first substrate and the electrically conductive structure and additionally, or alternatively, the second substrate may have a second feedthrough between a main side of the second substrate facing away from the second cavity and the electrically conductive structure. A feedthrough may be understood to mean a further perforation or an opening. Using this embodiment, an electrical connection of the electrically conductive structure to a voltage source situated outside of the apparatus may be effected in a simple manner. Optionally, one of the feedthroughs or both feedthroughs may be metallized in order to provide even more multifaceted connection options.

In accordance with one embodiment, the apparatus may comprise a further conductive structure, the further conductive structure possibly being arranged at the base of the second cavity. This embodiment increases the application options for the apparatus; for example, one of the conductive structures may be used for heating purposes, for example to perform a PCR, and the other may be used e.g. for electrical lysis.

Furthermore, the apparatus may comprise a lysate receiving region for receiving a lysate obtained during the lysis of the organic cells. The lysate receiving region may be arranged adjacent to the first fluid channel and/or the second fluid channel at the main side of the first substrate. Using this embodiment, cell constituents lysed in the apparatus may advantageously be supplied to a further diagnosis along the shortest path. The problems accompanying a long transport path, such as a reduction in the amount of lysate on account of e.g. dead volumes or a contamination of the lysate, may be thus avoided in a simple manner.

Furthermore, an analysis system for analyzing a biological sample is presented, the analysis system comprising the following features:

an apparatus for processing the biological sample of organic cells in accordance with a variant presented here; and a detection unit for detecting a predetermined cell constituent of the biological sample extracted from the organic cells in the apparatus, the detection unit being fluidically coupled to the apparatus.

In accordance with one embodiment, the detection unit may comprise a layer structure made of a first polymer substrate comprising a channel system, a second polymer substrate comprising a recess and a microfluidic layer arranged between the first polymer substrate and the second polymer substrate and comprising a microfluidic network, and also an analysis cavity, coupled to the channel system, for performing an analysis method on the lysate obtained in the apparatus. Here, the apparatus may be arranged in the recess and adjacent to the microfluidic layer in such a way that the lysate receiving region lies in the analysis cavity and the first fluid channel and/or the second fluid channel is fluidically coupled to the channel system. This embodiment facilitates the realization of the analysis system with low costs since it is possible to manufacture the detection unit, which has a simple structure and is usable in a flexible manner, with low production costs in large quantities.

In accordance with one embodiment, the analysis cavity may be formed by a passage opening in the microfluidic layer. As a result, the analysis system may be realized in a particularly space-saving manner.

In accordance with a further embodiment, the analysis cavity may be formed by a hollow in the first polymer substrate. In this embodiment, the analysis cavity may be coupled to the channel system of the first polymer substrate in a particularly simple manner.

Furthermore, a method for processing a biological sample is presented, the method comprising the following step:

moving the biological sample between a first cavity, which is laid out in a first substrate and forms a first chamber portion of a chamber for receiving the biological sample, and a second cavity, which is laid out in a second substrate and forms a second chamber portion of the chamber, through a filter element, which comprises a plurality of perforations embodied between the first cavity and the second cavity, and an electrically conductive structure arranged at the filter element in order to hold back a plurality of organic cells of the biological sample on the plurality of perforations; and applying at least one electric voltage to the electrically conductive structure in the presence of a lysing agent flushed into the chamber in order to lyse the plurality of organic cells held back at the plurality of perforations.

The method may be carried out in an apparatus for processing a biological sample in accordance with one of the embodiments explained above. This embodiment variant of the disclosure in the form of a method also allows the object underlying the disclosure to be achieved in a quick and efficient manner.

In accordance with one embodiment of the disclosure, the electric voltage may be applied in the applying step via a first conductor track connecting a first connection region of the electrically conductive structure with a second connection region of the electrically conductive structure in order to thermally lyse the plurality of organic cells held back at the plurality of perforations on the basis of Joule heating of the filter element. In this way, heating which is easily implementable from a technical point of view may be undertaken at the plurality of perforations.

In accordance with a further embodiment, a further electric voltage may be applied in the applying step via a second conductor track connecting a third connection region of the electrically conductive structure to a fourth connection region of the electrically conductive structure in order to electrically lyse the plurality of organic cells held back at the plurality of perforations on the basis of generating an electric field between the first conductor track and the second conductor track. Such an embodiment of the approach presented here offers the advantage of a particularly efficient lysis of cells in the perforations with small installation space requirements of the lysis structure employed.

Furthermore, the method may comprise a step of renewed application of the electric voltage to the electrically conductive structure. Thus, a plurality of cell constituents released from the plurality of organic cells during lysis may be duplicated if a reaction agent is present in the chamber. Since this embodiment allows a change of location between lysis and duplication of the substances to be examined to be avoided, the risks of contamination or of a loss of part of the lysate on account of dead volumes during the transfer may be eliminated.

BRIEF DESCRIPTION OF THE DRAWINGS

The approach presented here is explained in more detail below in an exemplary manner on the basis of the attached drawings. In detail.

DETAILED DESCRIPTION

In the following description of expedient exemplary embodiments of the present disclosure, the same or similar reference signs are used for the elements which are depicted in the various figures and have a similar effect, with a repeated description of these elements being dispensed with.

Figure 1:
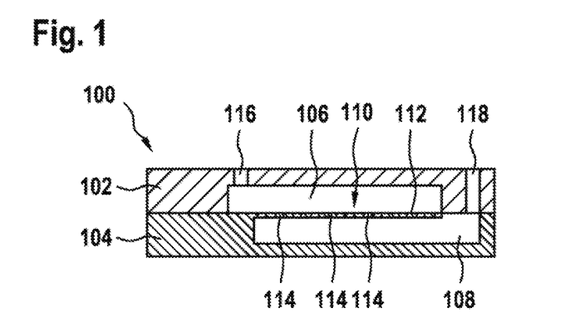
FIGS. 1 to 5 show cross-sectional views of an apparatus in accordance with exemplary embodiments of the present disclosure for processing a biological sample.

FIG. 1 shows a cross section through an exemplary basic embodiment, of an apparatus 100, presented herein, for processing a biological sample (which may also be referred to as analysis sample). The apparatus 100 is a layer structure made of two substrates 102 and 104, each with a recess or cavity 106 and 108, respectively, and an electrically conductive structure not shown here. The cavities 106 and 108 form partial chambers or chamber portions of a common chamber 110 for receiving the biological sample in the apparatus 100. A filter element 112 in the form of a membrane with a plurality of perforations or filter pores 114 is embodied within the second substrate 104 in the exemplary embodiment of the apparatus 100 shown in FIG. 1; however, it may also be formed within the first substrate 102. The recesses or partial chambers 106 and 108 each have a fluidic access in the form of a first fluid channel 116 and a second fluid channel 118.

In the shown exemplary embodiment of the apparatus 100, the substrates 102, 104 consist of silicon. A wafer-based etching process such as dry etching, e.g. deep reactive ion etching (DRIE), or, alternatively, a wet chemical method such as KOH etching was used to produce the recesses 106, 108 and filter pores 114. A conventional wafer bonding method, e.g. anodic bonding, eutectic bonding or silicon fusion bonding, was used for connecting the substrate layers 102, 104.

By way of example, the apparatus 100 is used to process a sample of organic material, such as e.g. a blood sample, for a subsequent analysis, e.g. in view of pathogens contained in the sample. Thus, the perforations 114 embodied in the filter element 112 may have suitable dimensions in order to hold target cells contained in the sample back at the filter element 112 and thus filter them out of the sample. The target cells thus concentrated at the filter membrane 112 may subsequently be lysed using the electrically conductive structure not shown in FIG. 1, for example in order to release a nucleic acid, required for the analysis, from the cell material. The lysis of the target cells may be undertaken in the form of a thermal and/or an electrical lysis by applying an electric voltage to the electrically conductive structure. Since all steps of cell processing are performed in the same chamber in the apparatus 100, the apparatus 100 may also be referred to as a so-called single chamber LOC.

Figure 2:
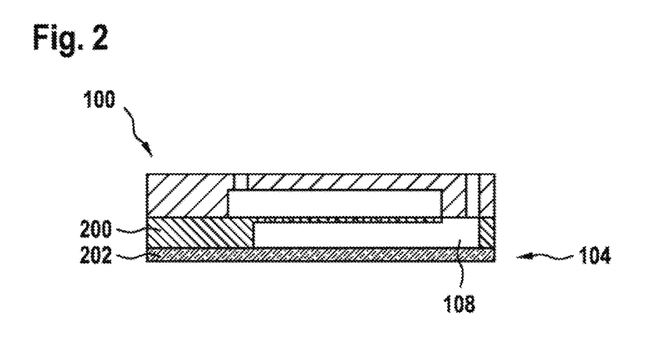

FIG. 2 shows a cross section through a further exemplary embodiment of the apparatus 100, which is characterized by the peculiarity that the second substrate 104 is composed of two layers or two substrate portions 200 and 202. This exemplary embodiment of the apparatus 100 is advantageous, in particular, in that more cost-effective process steps may be used for structuring the second cavity 108 in the first substrate portion 200, while the second substrate portion 202 consists of an unstructured wafer. By way of example, the second substrate portion 202 may also consist of glass. The optical access arising as a result thereof may, for example, be used for process monitoring.

Figure 3:
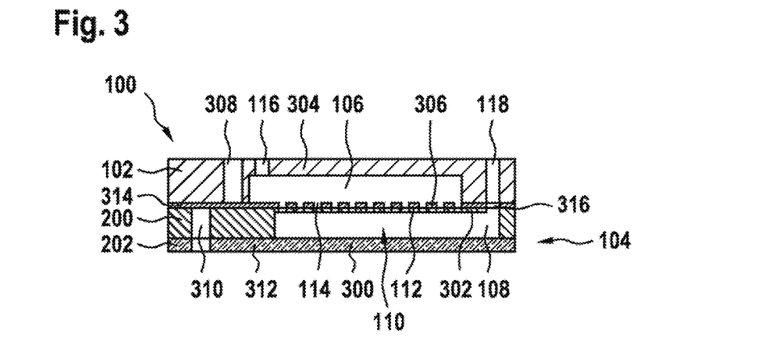

FIG. 3 shows the apparatus 100 in more detail on the basis of a further exemplary cross section. As shown in the illustration, the first substrate 102 and the second substrate 104 may (without loss of generality) be embodied as layers or plates with the same thickness, with, in the exemplary embodiment shown here too, the second substrate 104 being composed of the first substrate portion 200, which has the second cavity 108, and the second substrate portion 202, which forms a base of the apparatus 100 in this case. Therefore, a side of the second substrate portion 202 facing the chamber 110 forms a wall 300 of the chamber 110—in this case a wall delimiting the chamber 110 to the bottom. The chamber portions of the chamber 110 formed by the cavities 106, 108 are arranged offset to one another such that a portion of the first cavity 106 lies opposite a solid region of the second substrate 104 and a portion of the second cavity 108 lies opposite a solid region of the first substrate 102. The filter element 112 is formed by a portion of a main side 302 of the second substrate 104 facing the first substrate 102, which portion was left standing during the production process of the second cavity 108. Here, a main side should be understood to mean a side of the elements 102, 104 forming the layer structure 100 which has the greatest dimensions. On account of the very small thickness of this portion left standing and the multiplicity of perforations generated in the production process, the filter element 112 is embodied as a membrane in this case.

As the illustration in FIG. 3 shows, the first fluid channel 116 extends between a main side 304 of the first substrate 102 facing away from the first cavity 106 and the first cavity 106. The second fluid channel 118 extends from the main side 304 of the first substrate 102 to the second cavity 108 through the solid region of the first substrate 102 lying opposite the second cavity 108. In the shown exemplary embodiment, the biological sample is admitted into the first chamber portion 106 of the chamber 110 through the first fluid channel 116, flows through the filter element 112 in the second chamber portion 108 of the chamber 110 and is guided out of the chamber 110 again by way of the second fluid channel 118, for example using a pump.

In particular, FIG. 3 shows an electrically conductive structure 306, which consists of metal in the exemplary embodiment shown in FIG. 3, arranged between the first substrate 102 and the second substrate 101. In accordance with exemplary embodiments, it is also possible to use other electrically conductive materials. As shown in the illustration of FIG. 3, the electrically conductive structure 306 adjoins the filter element 112—here at an upper side of the filter membrane 112 formed from the second substrate 104—and extends parallel to the main sides 302 and 304 so that the perforations 114 remain exposed for the filter function of the membrane 112. The first substrate 102 has a first feedthrough 308 between the main side 304 of the first substrate 102 and the electrically conductive structure 306. The second substrate 104 has a second feedthrough 310 between a main side 312 of the second substrate 104 facing away from the second cavity 108 and the electrically conductive structure 306. The electrically conductive structure 306 is contacted electrically by way of the feedthroughs 308, 310 in order to supply the former with electric voltage.

Furthermore, the exemplary apparatus 100 shown in FIG. 3 has a compensation layer 314. The compensation layer 314 is arranged laterally adjoining the electrically conductive structure 306 between the first substrate 102 and the second substrate 104 and has an opening 316 in the region of the second fluid channel 118 for passage of the sample fluid.

In accordance with exemplary embodiments of the apparatus 100, the thickness of the electrically conductive layer 306 is 10 nm to 10 µm, preferably 100 nm to 1 µm. In the case of a very thin electrically conductive layer 306, conventional wafer bonding methods may continue to be used without the additional compensation layer 314. The additional compensation layer 314 is introduced for a thicker electrically conductive layer 306, as shown in an exemplary manner in FIG. 3. By way of example, the compensation layer 314 is formed of glass seal.

Depending on the configuration of the electrically conductive layer 306, one of the two accesses 308, 310 is sufficient for contacting the electrically conductive layer 306, and so the other one may be dispensed with. By way of example, spring contact pins may be used for contacting the electrically conductive layer 306. The access 308 is advantageous in that a perforation required to lay out the access 308 may easily be produced in the first substrate 102 since said perforation extends through the entire component 102. The access 310 is advantageous in that a spring contact pin inserted into the second feedthrough 310 acts in the direction of the bond connection to the microfluidic component in the case of a possible subsequent integration of the apparatus 100 in a polymer microfluidic environment and the mechanical load on the bond connection is reduced as a result thereof.

In accordance with alternative exemplary embodiments of the apparatus 100, walls of the feedthroughs 308, 310 over electrical contact points of the electrically conductive layer 306 may be filled with an electrically conductive material such that a new contact point arises on the outer sides 304 and 312 of the component 100. This is advantageous, in particular, in that, in addition to spring contact pins, further electrical interfaces may also be used for contacting the electrically conductive layer 306, for example sliding contacts.

Figure 4:
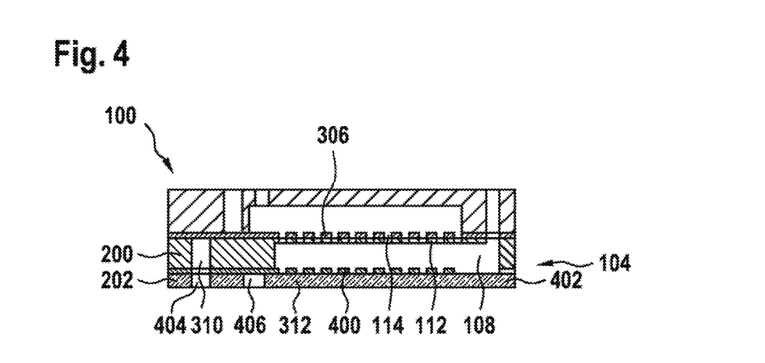

FIG. 4 shows a cross section of a further exemplary embodiment of the apparatus 100. This exemplary embodiment has the peculiarity of a further electrically conductive structure 400 and a further compensation layer 402. In the exemplary embodiment of the apparatus 100 shown in the illustration of FIG. 4, the further electrically conductive structure 400 is arranged between the first substrate portion 200 and the second substrate portion 202 of the second substrate 104 and adjoins the main side of the second substrate portion 202 forming the base 300 of the second cavity 108. The further compensation layer 402 is arranged laterally adjoining the further electrically conductive structure 400 between the first substrate portion 200 and the second substrate portion 202 of the second substrate 104 and has a further opening 404 in the region of the second feedthrough 310 for electrically contacting the first electrically conductive layer 306.

In the exemplary embodiment of the apparatus 100 shown in FIG. 4, the first electrical access for contacting the electrically conductive structure 306 is dispensed with. Instead, there is a third feedthrough 406 between the main side 312 of the second substrate 104 facing away from the second cavity 108 and the further electrically conductive structure 400 for the purposes of contacting the further electrically conductive structure 400. The exemplary embodiment of the apparatus 100 shown in FIG. 4 is characterized by the advantage that, for example, a heating function for heating the filter element 112 may be transferred to the further or lower structure 400 and hence a greater degree of freedom of design arises for the electrically conductive layer 306. As a result of this, it is possible, for example, to use a very high pore density of the filter membrane 112 and nevertheless position a conductor track region for lysis with electric fields at each pore or each perforation 114. The conductor track regions will still be discussed in more detail on the basis of FIG. 6 below.

Figure 5:
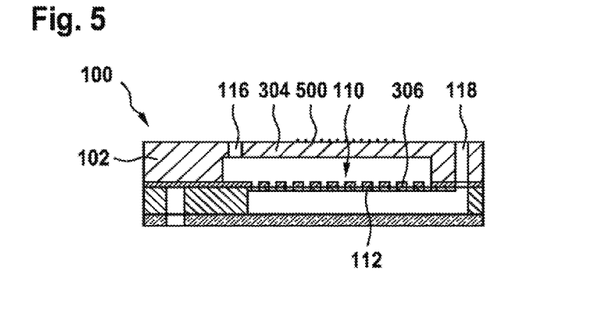

On the basis of a further cross sectional illustration, FIG. 5 shows a particular embodiment in which the apparatus 100 was augmented by a detection region 500 for receiving a lysate obtained during lysis of cells in the chamber 110. As shown in the illustration of FIG. 5, the detection region 500 is situated between the first fluid channel 116 and the second fluid channel 118 on the outer side or main side 304 of the first substrate 102. In the shown exemplary embodiment, the detection region or detection region 500 is formed by biochemical capture molecules which were immobilized on the main side 304. The biochemical capture molecules are, for example, proteins, antibodies or DNA in the form of a microarray.

This exemplary embodiment of the apparatus 100 shown in FIG. 5 is advantageous, in particular, in that a liquid processed in the chamber 110 may be output directly onto the detection region 500 from the filter 112 by way of one of the two fluid channels 116, 118 in combination with an appropriate microfluidic environment as presented below on the basis of FIGS. 7 and 8. On the one hand, this results in a very short transportation path for the liquid. On the other hand, the heating function integrated into the component 100—in this case by way of the electrically conductive layer 306—may be used to set a suitable temperature for a detection reaction of the liquid.

An exemplary thickness of the substrates 102 and 104 of the exemplary embodiments of the apparatus 100 shown in FIGS. 1 to 5 is 10 to 3000 µm, preferably 100 to 1000 µm. An exemplary thickness of the filter membrane 110 lies between 0.1 and 500 µm, preferably between 10 and 200 µm. An exemplary lateral dimension of the filter membrane 112 is 1 to 20 mm, preferably 5 to 10 mm. An exemplary diameter of the perforations or pores 114 of the filter element 112 lies between 0.1 and 100 µm, preferably between 0.2 and 20 µm. An exemplary density of the pores 114 lies between $10^5$ and $10^9$ pores per square centimeter of the filter membrane 112.

Figure 6:
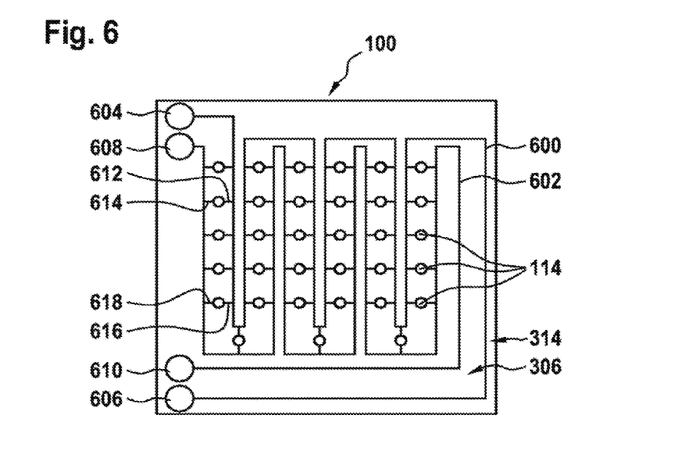
FIG. 6 shows a plan view of an electrically conductive structure of an apparatus in accordance with one exemplary embodiment of the present disclosure for processing a biological sample.

FIG. 6 shows a longitudinal section through an exemplary embodiment of the apparatus 100, allowing a plan view of the plane of the layer structure formed by the electrically conductive structure 306 and the compensation layer 314. As shown in the illustration of FIG. 6, the electrically conductive structure 306 comprises a first conductor track 600 and a second conductor track 602. The first conductor track 600 extends in a first meandering structure between a first connection region 604 and a second connection region 606 of the electrically conductive structure 306. The second conductor track 602 extends in a second meandering structure parallel to the first meandering structure between a third connection region. 608 and a fourth connection region 610 of the electrically conductive structure 306. A first voltage is applied to the first conductor track 600 between the first connection region 604 and the second connection region 606 and a second voltage is applied to the second conductor track 602 between the third connection region 608 and the fourth connection region 610. The first voltage and second voltage may be the same or different.

The electrically conductive structure 306 is embedded into, or surrounded laterally by, the compensation layer 314 such that the filter membrane arranged below the layers 306 and 314 is completely covered, with suitably positioned openings of the compensation layer 314 exposing the perforations 114 of the filter element for the passage of the sample liquid.

In particular, what is visible from the illustration of FIG. 6 is that the first conductor track 600 and the second conductor track 602 extend along rows of the perforations 114, laid out in the form of a grid, of the filter element of the apparatus 100 arranged below the electrically conductive layer 306 in this case. The first conductor track 600 extends on one side of each row of perforations 114 at a predetermined distance from an edge region 612 of in each case one of the perforations 114 and the second conductor track 602 extends on the other side of each row of perforations 114 at the same predetermined distance from a further edge region 614, lying opposite the edge region 612, of in each case one of the perforations 114.

In the exemplary embodiment of the apparatus 100 shown in FIG. 6, the first conductor track 600 has a multiplicity of first conductor track portions 616 and the second conductor track 602 has a multiplicity of second conductor track portions 618, with the multiplicity of the first conductor track portions 616 and the multiplicity of the second conductor track portions 618 corresponding in terms of the number thereof to the number of the multiplicity of perforations 114 of the filter element. As shown in the illustration of FIG. 6, one of the first conductor track portions 616 in each case extends to the edge region 612 of in each case one of the perforations 114 and one of the second conductor track portions 618 in each case extends to the further edge region 614 of in each case one of the perforations 114.

In the example embodiment of the apparatus 100 shown in FIG. 6, the electrically conductive layer 306 arranged over the filter membrane consists of a metal, in particular copper, aluminum, titanium, platinum or gold. The electrically conductive layer 306 is structured in such a way that the four connection regions 604, 606, 608 and 610 emerge. Here, the first conductor track 600 is structured in such a way that the connection regions 601 and 606 are electrically connected to one another. The further or second conductor track 602 connects the connection regions 608 and 610. At the same time, the conductor tracks 600 and 602 are laid out between the perforations or pores 114 of the filter element in such a way that a path, which is as long as possible, with a high electrical resistance emerges. In this way, a heating function in the electrically conductive layer 306 may be realized by the generation of Joule heating for the purposes of heating the adjacent filter element, for example for thermal lysis of filtered cells or for heating the entire system 100 for a PCR reaction, by applying a voltage between the connection regions 604 and 606, and 608 and 610.

By shorting the connection regions 604 and 606 and the connection regions 608 and 610, and subsequently applying a voltage between the combined regions 604, 606 and 608, 610, an electric field may be generated between conductor track regions or conductor track portions 616 and 618 respectively lying opposite one another, said electric field in each case extending over a pore 114. By means of this electric field, it is possible to lyse a cell situated in the region of the pore 114. Here, use may be made, alternatively, of both static electric fields and alternating electromagnetic fields with field strengths of 1 kV/cm to 1000 kV/cm. The type of structuring of the electrically conductive layer 306 shown in FIG. 6 is particularly advantageous as very high fields may be generated even at low voltages on account of the short distance between the conductor track regions 616, 618. Furthermore, a mixed operation of the two described lysis methods is possible, i.e. a thermal lysis in combination with a lysis with electric or electromagnetic fields, as a result of which the lysis yield may be further increased.

In the structure 100 shown in the longitudinal section in FIG. 6, it is possible to hold relevant sample constituents, e.g. particles, in particular cells, for example bacteria or circulating tumor cells (CTCs), back on the filter by a suitable adaptation of the pore dimensions of the perforations 114. The metallic structures 600, 602, 616, 618 may subsequently be used as heating structures for performing a PCR.

Figure 7:
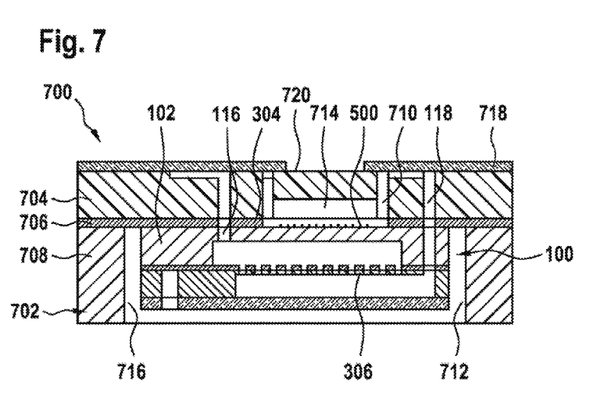
FIGS. 7 and 8 show cross-sectional views of an analysis system in accordance with exemplary embodiments of the present disclosure for analyzing a biological sample.

FIG. 7 shows a cross-sectional view of an exemplary embodiment of an analysis system 700, proposed herein, for analyzing a biological sample. The analysis system 700 incorporates the apparatus 100, in particular the exemplary embodiment of the apparatus 100 presented on the basis of FIG. 5, which was augmented by the detection region 500. In addition to the apparatus 100, the analysis system 700 comprises a detection unit 702 for detecting a predetermined cell constituent of the biological sample released from organic cells in the apparatus 100.

As the illustration in FIG. 7 shows, the detection unit 702 forms a layer structure made of a first polymer substrate 704, a microfluidic layer 706 and a second polymer substrate 708. The first polymer substrate 704 comprises a channel system 710, which couples to the fluid channels 116, 118 and therefore fluidically connects the apparatus 100 to the detection unit 702. The microfluidic layer 706 is arranged between the first polymer substrate 704 and the second polymer substrate 708 and has a microfluidic network not explicitly shown in the illustration. The second polymer substrate 708 has a recess 712 directed to the microfluidic layer 706, in which the apparatus 100 is arranged in such a way that the first substrate 102 of the apparatus 100 adjoins the microfluidic layer 706. Furthermore, the detection unit 702 comprises an analysis cavity 714, fluidically coupled to the channel system 710, for performing an analysis method on a lysate obtained in the apparatus 100. In the exemplary embodiment of the analysis system 700 shown in FIG. 7, the analysis cavity 714 is embodied in the form of a hollow in the first polymer substrate 704. As is easily visible from the illustration in FIG. 7, the apparatus 100 is arranged in the recess 712 and adjoining the microfluidic layer 706 in such a way that the detection region 500 lies in the analysis cavity 714 and the first fluid channel 116 and the second fluid channel 118 are fluidically coupled to the channel system 710.

By way of example, the polymer substrate 704 is formed from PC, PP, PE, COP, COC or PMMA and separated from the further polymer substrate 708 by the intermediate layer or microfluidic layer 706. The microfluidic layer 706 may likewise consist of a polymer, in particular a thermoplastic elastomer, and be embodied as a hot melt adhesive film or double-sided adhesive film. The recess 712 allowing the component or the apparatus 100 to be brought into contact with the intermediate layer 706 is situated in the further or second polymer substrate 708. Here, the recess 712 is configured in such a way that a gap 716 with a width of 0.1 mm to 10 mm, preferably from 2 mm to 5 mm, arises around the component 100. The gap 716 allows quick cooling of the component 100 by means of an air cooling supplied from the outside. As a result, fast process times are achieved, in particular in combination with a PCR.

It is possible to connect the apparatus 100 in a mechanically secure and fluidically tight manner to the layer structure consisting of the polymer substrate 704 and the intermediate layer 706 by means of suitable methods, e.g. laser transmission welding or laser transmission bonding, thermal bonding or ultrasound welding. In this way, the component 100 may be integrated into the polymer layer structure 702 in a cost-effective manner, permitting the provision of microfluidic functions such as valves and pumps with the aid of the flexible intermediate layer 706. Surface treatments or additional auxiliary layers, for example plasma or HDMS treatments and photoresist layers, may be used on the contact side 304 of the apparatus 100 for the purposes of improving the adherence between the apparatus 100 and the intermediate layer 706.

The analysis cavity 714, which is connected to the microfluidic channels 710 in such a way that the analysis cavity 714 is connected to the microfluidic network of the intermediate layer 706 on one side and to the fluid channel 118 on the other side, is situated within the first polymer substrate 704. In the exemplary embodiment of the analysis system 700 shown in FIG. 7, the polymer substrate 704 is covered on the outside by a layer 718, e.g. a polymer or an adhesive film, in order to close the microfluidic channels 710 to the outside. An optical access to the cavity 714 is provided in a particularly advantageous manner, specifically in the form of a recess 720 in the layer 718 in the exemplary embodiment of the analysis system 700 shown in FIG. 7. In accordance with an alternative exemplary embodiment, the layer 718 may, instead, have an embodiment which is transparent in the region of the analysis cavity 714 or transparent everywhere.

Using the structure 700 shown in an exemplary manner in FIG. 7, it is possible to bring a reaction product into contact with the detection region 500 by way of the fluid channel 118, for example using a microfluidic pump (not shown here), after all reactions within the apparatus 100 are completed and thus start a detection reaction. In this case, the heaters integrated in the component 100 by way of the electrically conductive layer 306 may be used to provide a suitable temperature during the detection reaction.

Figure 8:
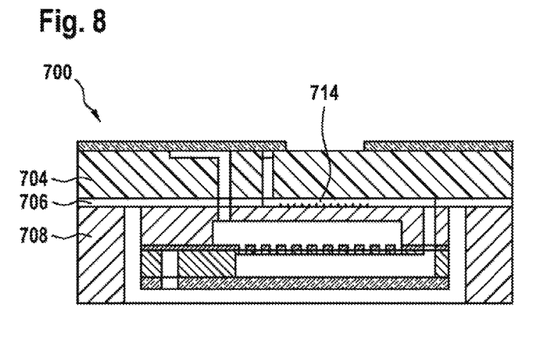

In a further cross-sectional view, FIG. 8 shows a further exemplary embodiment of the analysis system 700, which is similar to the embodiment shown in FIG. 7. As a main difference, the analysis cavity 714 in the exemplary embodiment of the analysis system 700 shown in FIG. 8 is not taken out of the first polymer substrate 704 but instead formed as a recess or passage opening in the microfluidic layer 706. An advantage of this embodiment, in particular, is that the height of the cavity 714 may be set very accurately by way of the thickness of the intermediate layer 706. In particular, very low heights may be realized, as a result of which the dead volume is reduced and hence the sensitivity of the detection reaction is increased.

An exemplary thickness of the polymer substrates 704, 708 is 0.1 to 10 mm, preferably 1 mm to 3 mm; an exemplary thickness of the intermediate layer 706 lies between 5 and 500 µm, preferably between 50 µm and 150 µm. Exemplary channel cross sections of the channel system 710 are $10 \times 10$ µm$^2$ to $3 \times 3$ mm$^2$, preferably $100 \times 100$ pm$^2$ to $1 \times 1$ mm$^2$. Lateral dimensions of the overall analysis system 700 lie between $10 \times 10$ and $200 \times 200$ mm$^2$, preferably between $30 \times 30$ mm$^2$ and $100 \times 100$ mm$^2$.

Figure 9:
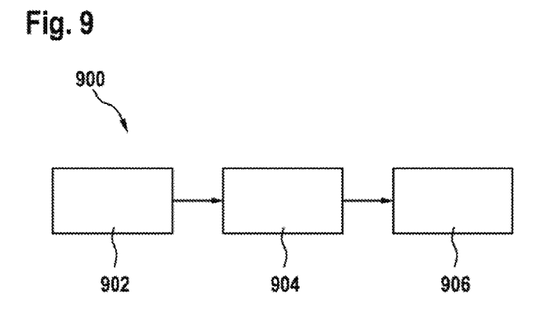
FIG. 9 shows a flowchart of an approximate procedure of a method in accordance with one example embodiment of the present disclosure for processing a biological sample.

FIG. 9 shows a schematic procedure of an exemplary embodiment of a method 900 for processing a biological sample. The method 900 may be carried out in a single chamber LOC with a filter membrane integrated in a PCR chamber, as is presented on the basis of FIGS. 1 to 5. The chamber has a fluidic inlet and outlet and, additionally, an electrically conductive layer. Expressed in a very abbreviated manner, the method 900 progresses in such a way that a fluidic sample is flushed through the filter situated in the chamber in order to filter out and fix target cells. After washing the filter, a PCR reaction mixture is flushed in and the fluidic entrances and exits of the chamber are sealed. The cells situated on the filter are lysed either thermally or electrically by means of the electrodes. DNA sections from the broken-open cells are subsequently amplified in the same chamber. The temperature cycles required to this end are provided by the electrodes acting as resistive heaters.

The method 900 may be subdivided roughly into three relevant process portions. A first process portion of isolating cells or target cells from the biological sample comprises a step 902 of moving the biological sample from a first chamber portion of the chamber into a second chamber portion of the chamber, through a filter element formed between the first chamber portion and the second chamber portion and an electrically conductive structure arranged on the filter element, in order to hold a multiplicity of cells of the biological sample hack on a multiplicity of perforations in the filter element. A second process portion of breaking open or lysing the target cells comprises a step 904 of applying an electric voltage to the electrically conductive structure arranged at the filter element in the presence of a lysis agent flushed into the chamber in order to electrically or thermally lyse the multiplicity of cells held back at the multiplicity of perforations. A third process portion of amplifying or duplicating a cell substance, such as e.g. DNA, extracted from the cells in step 904 comprises a step 906 of renewed application of the electric voltage to the electrically conductive structure in order to duplicate a multiplicity of cell constituents, released from the cells, in the chamber in the presence of a reaction agent.

Figure 10:
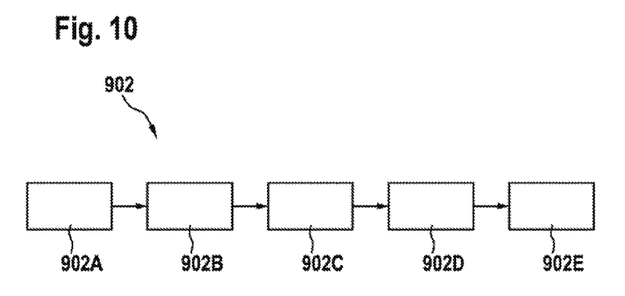
FIG. 10 shows a flowchart of a process portion of the filtration of the method from FIG. 9 in accordance with one example embodiment of the present disclosure.

FIG. 10 schematically shows a subdivision of the first process portion of the method 900, characterized by the step 902 in which the filtration of the analysis sample occurs, into individual partial sequences in accordance with one exemplary embodiment of the present disclosure. A partial sequence 902A characterizes an initial state, in which the sample solution with the target cells was admitted into the first chamber portion of the chamber by means of a fluid channel and said sample solution is present there for further processing. An addition of a thinning or separation buffer is carried out in the chamber in a partial sequence 902B. The sample solution is moved or flushed through the filter between the first chamber portion and the second chamber portion in a partial sequence 902C. Inhibitors and background DNA are flushed out of the sample solution in a partial sequence 902D. A partial sequence 902E characterizes a final state of the first process portion, in which the target cells are fixed to the filter membrane.

The object of the first process portion broken down in FIG. 10 lies in fixing target cells, for example pathogens or circulating tumor cells, on the filter membrane and simultaneously removing PCR inhibitors such as e.g. hemoglobin and other unwanted cells. Here, the dimensions of the pores of the filter membrane depend on the specific application. Thus, pore dimensions between 0.2 and 1.0 µm are required for the filtration of bacteria and fungi and pore dimensions between 5 µm and 30 µm are required for the filtration of circulating tumor cells.

The eukaryotic cells are initially lysed in the case where the target cells are pathogens such as bacteria or fungi. By way of example this may be effected by means of chaotropic salts. There is no need to perform such a sample preparation if the target cells are tumor cells. Reagents improving the fluidity of the sample or promoting the separation of the target cells may be additionally added to a sample solution. Such a sample solution is then flushed through the filter. Here, the pore dimensions are selected in such a way that the target cells remain stuck in the pores of the filter and the other constituents—the cell remains of the lysed eukaryotic cells in the case of pathogens; all healthy cells, and hence cells with normal dimensions, in the case of tumor cells— are flushed through the pores. Subsequently, the constituents adhering to the filter are flushed with a washing buffer. As a result of this method step 902, the target cells of the sample solution are fixed on the filter and the unwanted and/or interfering substances of the sample solution are flushed away or removed.

Figure 11:
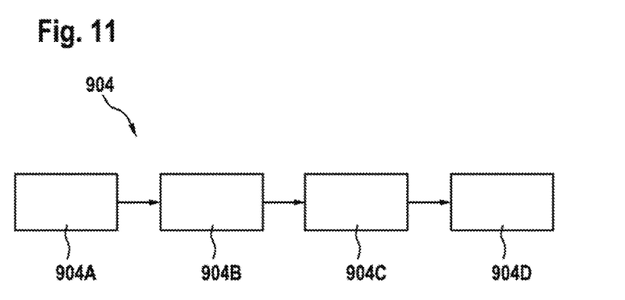
FIG. 11 shows a flowchart of a process portion of the electric and/or thermal lysis of the method from FIG. 9 in accordance with one example embodiment of the present disclosure.

FIG. 11 schematically shows a breakdown, in individual partial sequences, of the second process portion of the method 900, characterized by the step 904, in which the electrical and/or thermal lysis of the analysis sample is carried out, in accordance with one example embodiment of the present disclosure. A partial sequence 904A characterizes an initial state, in which the target cells are fixed to the filter element. In a partial sequence 904B, the filter element with the target cells fixed thereon is flushed with a lysis medium. A thermal and/or electrical lysis of the cells is then carried out in a partial sequence 904C. Finally, a partial sequence 904D characterizes a final state of the second process portion, in which the broken-up cells are present.

The goal of this second process portion shown in figure lies in the breaking open of the cells which are fixed on the filter and surrounded by an aqueous medium. The medium with which the filter containing the fixed target cells is flushed in the partial sequence 904B may either be a PCR reaction mix, which contains all PCR reaction components, or water in order to take up PCR reaction components stored in the vicinity of the membrane. Here, the PCR reaction components may be stored in a freeze-dried (lyophilized) state or alternatively embedded in paraffin. The reaction mix required for a PCR then sets in by mixing the reaction components with water, specifically by rehydration in the case of the freeze-dried stored PCR reaction components and by melting of the paraffin in the case of the PCP reaction components embedded in paraffin.

In the partial sequence 904C, the cells are lysed in the medium as described above. This may be carried out thermally by heating the filter membrane and/or the surrounding medium to 80° C. to 120° C., preferably to 90° C. to 100° C. Preferably, a so-called hot start polymerase is used in the partial sequence 904C. The thermal lysis then additionally has the advantage that, in this case, the polymerase is activated at the same time. The target cells may also be lysed by applying an electric field. Here, use may be made of either an alternating electric field of e.g. $0.1 \times 10^6$ V/m to $10 \times 10^6$ V/m or a constant electric field or a combination of both. After the lysis, the medium in partial sequence 904D contains the cellular DNA of the lysed cells, remains of the cells and, additionally, all components for a PCR to be performed in the third process portion.

Figure 12:
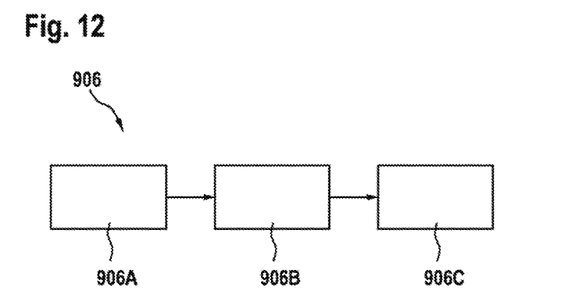
FIG. 12 shows a flowchart of a process portion of the amplification of target cells of the method from FIG. 9 in accordance with one example embodiment of the present disclosure.

FIG. 12 schematically shows a breakdown, in individual partial sequences, of the third process portion of the method 900 characterized by the step 906, in which the duplication or amplification of the DNA extracted from the cells is carried out, in accordance with one example embodiment of the present disclosure. A partial sequence 906A characterizes an initial state, in which the broken-up cells are present. In a partial sequence 906B, there is a biochemical reaction, in this case a PCR. Finally, a partial sequence 906C characterizes a final state of the third process portion, in which the duplicated DNA sections are present.

The goal of this third process portion shown in FIG. 12 lies in the amplification of specific sections of the cellular DNA. Here, the amplification takes place in the presence of the filter. The medium which contains the cellular DNA of the lysed cells is preferably a PCR reaction mix. By applying temperatures that alternate between 50° C. and 95° C. to the medium, a FOR is performed in the partial sequence 906B. By way of example, the individual PCR products are identified in another region to that of the filter. To this end, two methods may be used in principle.

A microarray-based detection is carried out in a first method. Here, the aforementioned PCR is e.g. an asymmetric multiplex PCR. Use is made of between 1 and 20 primer pairs, and between 20 and 50 PCR temperature cycles are performed. The primers are marked by a fluorophore. Hence, the PCR products carry a fluorescent label and generate detectable signals on the microarray. Hence, qualitative deductions about the presence of specific DNA sections in the sample solution are possible. A second method is referred to as nested PCR. Here, the aforementioned PCR is a multiplex PCR. Use is made of between 1 and 500 primer pairs, preferably between 1 and 50 primer pairs, and between 10 and 40 PCR temperature cycles are performed. The PCR products of the first PCR are diluted and divided among separate reaction chambers, with 1-4 primer pairs being stored in each chamber. A second PCR reaction is performed in these chambers. The increase of signals from these reactions is detected in real time, which is why such a PCR may also be referred to as "real-time PCR". This allows quantitative deductions to be drawn about the presence of specific DNA sections in the sample solution.

The concept provided herein of cell processing and/or diagnosis using a combination, arranged in a chamber, of filter element and electrically conductive structure may be used for analysis systems, in particular for microfluidic lab on-a-chip systems, for environmental analysis or for medical diagnostics.

The exemplary embodiments described and shown in the figures have only been selected in an exemplary manner. Different exemplary embodiments may be combined completely or in relation to individual features. Also, one exemplary embodiment may be augmented by features of a further exemplary embodiment.

Furthermore, the method steps presented herein may be carried out repeatedly and in a sequence that differs from the one described here.

If an exemplary embodiment comprises an "and/or" link between a first feature and a second feature, this should be read in such a way that the exemplary embodiment, in accordance with one embodiment, has both the first and the second feature and, in accordance with a further embodiment, has either only the first feature or only the second feature.

The invention claimed is:

1. An apparatus for processing a biological sample, the apparatus comprising:
    a first substrate having a first cavity forming a first chamber portion of a chamber, the chamber configured to receive the biological sample;
    a second substrate having a second cavity forming a second chamber portion of the chamber;
    a filter element having a plurality of perforations, the filter element arranged between the first cavity and the second cavity and configured to hold back a plurality of organic cells of the biological sample at the plurality of perforations when moving the biological sample from the first cavity to the second cavity through the filter element; and
an electrically conductive structure arranged at the filter element and configured to bring about lysis of the plurality of organic cells as the plurality of organic cells are held back by the filter element and/or to duplicate and/or detect defined sections of exposed DNA, wherein
    the electrically conductive structure comprises a first conductor track between a first connection region of the electrically conductive structure and a second connection region of the electrically conductive structure, the first conductor track configured to apply a first voltage between the first connection region and the second connection region, and
    the electrically conductive structure comprises a second conductor track between a third connection region of the electrically conductive structure and a fourth connection region of the electrically conductive structure, the second conductor track configured to apply a second voltage between the third connection region and the fourth connection region.

2. The apparatus as claimed in claim 1, wherein the first substrate and the second substrate are at least partly formed from silicon.

3. The apparatus as claimed in claim 1, further comprising:

a first fluid channel extending between a main side of the first substrate and the first cavity, the main side of the first substrate facing away from the first cavity; and a second fluid channel extending between the main side of the first substrate and the second cavity, wherein one of the first fluid channel and the second fluid channel is configured to admit the biological sample into the chamber and the other of the first fluid channel and the second fluid channel is configured to release the biological sample from the chamber.

4. The apparatus as claimed in claim 3, wherein, for electrically contacting the electrically conductive structure, the first substrate has a first feedthrough between the main side of the first substrate and the electrically conductive structure and/or the second substrate has a second feedthrough between a main side of the second substrate facing away from the second cavity and the electrically conductive structure.

5. The apparatus as claimed in claim 3, further comprising a detection region configured to receive a lysate obtained during lysis of the organic cells, the detection region arranged adjacent to at least one of the first fluid channel and the second fluid channel at the main side of the first substrate.

6. The apparatus as claimed in claim 1, wherein:
the second substrate comprises a first substrate portion comprising the second cavity;
the second substrate comprises a second substrate portion arranged adjacent to a base of the second cavity forming a wall of the chamber; and
the first substrate portion is made of silicon and the second substrate portion is made of glass.

7. The apparatus as claimed in claim 6, further comprising a further conductive structure arranged at the base of the second cavity.

8. The apparatus as claimed in claim 1, wherein:
the first conductor track has at least one first conductor track portion and the second conductor track has at least one second conductor track portion;
the first conductor track portion extends to an edge of a perforation; and
the second conductor track portion extends to a further edge of the perforation, the further edge lying opposite the edge.

9. The apparatus as claimed in claim 1, wherein:
the first conductor track extends in a first meandering structure along the plurality of perforations of the filter element from the first connection region to the second connection region and the second conductor track extends in a second meandering structure complementary to the first meandering structure along the plurality of perforations of the filter element from the third connection region to the fourth connection region.

10. The apparatus as claimed in claim 1, wherein the filter element is formed from at least one of the first substrate and the second substrate.

11. The apparatus as claimed in claim 10, wherein the electrically conductive structure is positioned between the first cavity and the second cavity.

12. An analysis system for analyzing a biological sample, the analysis system comprising:
an apparatus configured to process the biological sample of organic cells, the apparatus including:
a first substrate having a first cavity forming a first chamber portion of a chamber, the chamber configured to receive the biological sample;
a second substrate having a second cavity forming a second chamber portion of the chamber;
a filter element having a plurality of perforations, the filter element arranged between the first cavity and the second cavity and configured to hold back a plurality of organic cells of the biological sample at the plurality of perforations when moving the biological sample from the first cavity to the second cavity through the filter element;
an electrically conductive structure arranged at the filter element and configured to bring about lysis of the plurality of organic cells as the plurality of organic cells are held back by the filter element and/or to duplicate and/or detect defined sections of exposed DNA;
a first fluid channel extending between a main side of the first substrate and the first cavity, the main side of the first substrate facing away from the first cavity, and a second fluid channel extending between the main side of the first substrate and the second cavity, wherein one of the first fluid channel and the second fluid channel is configured to admit the biological sample into the chamber and the other of the first fluid channel and the second fluid channel is configured to release the biological sample it from the chamber;
a detection region configured to receive a lysate obtained during lysis of the organic cells, the detection region arranged adjacent to at least one of the first fluid channel and the second fluid channel at the main side of the first substrate; and
a detection unit configured to detect a predetermined cell constituent of the biological sample extracted from the organic cells in the apparatus, wherein
the electrically conductive structure comprises a first conductor track between a first connection region of the electrically conductive structure and a second connection region of the electrically conductive structure, the first conductor track configured to apply a first voltage between the first connection region and the second connection region, and
the electrically conductive structure comprises a second conductor track between a third connection region of the electrically conductive structure and a fourth connection region of the electrically conductive structure, the second conductor track configured to apply a second voltage between the third connection region and the fourth connection region the detection unit fluidically coupled to the apparatus.

13. The analysis system as claimed in claim 12, wherein:
the detection unit comprises:
a layer structure made of:
a first polymer substrate comprising a channel system;
a second polymer substrate comprising a recess; and
a microfluidic layer arranged between the first polymer substrate and the second polymer substrate and comprising a microfluidic network; and
an analysis cavity, coupled to the channel system, for performing an analysis method on the lysate obtained in the apparatus, and
the apparatus is arranged in the recess and adjacent to the microfluidic layer such that the detection region lies in the analysis cavity and at least one of the first fluid channel and the second fluid channel is fluidically coupled to the channel system.

14. The apparatus of claim 12, wherein the filter element is formed from at least one of the first substrate and the second substrate.

15. A method for processing a biological sample, the method comprising:
   moving the biological sample between a first cavity and a second cavity through a filter element and an electrically conductive structure, the first cavity laid out in a first substrate and forming a first chamber portion of a chamber for receiving the biological sample, the second cavity laid out in a second substrate and forming a second chamber portion of the chamber, the filter element comprising a plurality of perforations embodied between the first cavity and the second cavity in order to hold back a plurality of organic cells of the biological sample at the plurality of perforations, the electrically conductive structure arranged at the filter element; and
   applying at least one electric voltage to the electrically conductive structure in the presence of a lysing agent flushed into the chamber by applying a first electric voltage via a first conductor track connecting a first connection region of the electrically conductive structure with a second connection region of the electrically conductive structure, and by applying a second electric voltage via a second conductor track connecting a thud connection region of the electrically conductive structure to a fourth connection region of the electrically conductive structure, thereby lysing the plurality of organic cells held back at the plurality of perforations.

16. The method as claimed in claim 15, wherein:
   applying the at least one electric voltage includes thermally lysing the plurality of organic cells held back at the plurality of perforations by Joule heating of the filter element.

17. The method as claimed in claim 15, wherein:
   applying the at least one electric voltage includes electrically lysing the plurality of organic cells held back at the plurality of perforations by generating an electric field between the first conductor track and the second conductor track while the plurality of organic cells are held back at the plurality of perforations.

18. The method as claimed in claim 15, further comprising:
   re-applying the at least one electric voltage to the electrically conductive structure to duplicate a plurality of cell constituents released from the plurality of organic cells during lysis when a reaction agent is present in the chamber.

19. The method of claim 15, wherein moving the biological sample between a first cavity and a second cavity through a filter element and an electrically conductive structure comprises:
   moving the biological sample between the first cavity and the second cavity through a filter element formed from at least one of the first substrate and the second substrate, and through an electrically conductive structure.

* * * * *

UNITED STATES PATENT AND TRADEMARK OFFICE
CERTIFICATE OF CORRECTION

PATENT NO. : 10,308,977 B2
APPLICATION NO. : 15/311142
DATED : June 4, 2019
INVENTOR(S) : Brettschneider et al.

It is certified that error appears in the above-identified patent and that said Letters Patent is hereby corrected as shown below:

In the Claims

Column 18, Line 26, Claim 12 "biological sample it from the" should read --biological sample from the--

Column 18, Line 35, Claim 12 "in the apparatus, wherein" should read --in the apparatus, the detection unit fluidically coupled to the apparatus, wherein--

Column 18, Lines 49 and 50, Claim 12 "the fourth connection region the detection unit fluidically coupled to the apparatus." should read --the fourth connection region.--

Column 19, Line 26, Claim 15 "connecting a thud" should read --connecting a third--

Signed and Sealed this
Fourteenth Day of January, 2020

Andrei Iancu
*Director of the United States Patent and Trademark Office*